(12) United States Patent
McDaniel

(10) Patent No.: US 7,104,982 B2
(45) Date of Patent: Sep. 12, 2006

(54) CATHETER GRIP

(76) Inventor: Benjamin D. McDaniel, 615 Marigold, Corona del Mar, CA (US) 92625

( * ) Notice: Subject to any disclaimer, the term of this patent is extended or adjusted under 35 U.S.C. 154(b) by 78 days.

(21) Appl. No.: 10/871,677

(22) Filed: Jun. 14, 2004

(65) Prior Publication Data

US 2005/0277909 A1 Dec. 15, 2005

(51) Int. Cl.
*A61M 25/16* (2006.01)

(52) U.S. Cl. ............................................. 604/533

(58) Field of Classification Search ............... 604/164, 604/167, 165, 171, 533–539, 523, 158, 159, 604/174, 178, 528, 177, 164.01–164.13, 604/165.01–165.04, 167.01–167.06; 600/585; 606/108
See application file for complete search history.

(56) References Cited

U.S. PATENT DOCUMENTS

| | | | |
|---|---|---|---|
| 2,234,686 A | | 3/1941 | Walter |
| 3,487,837 A | | 1/1970 | Petersen |
| 3,821,957 A | | 7/1974 | Riely et al. |
| 4,362,156 A | * | 12/1982 | Feller et al. ............. 604/165.03 |
| 4,985,018 A | | 1/1991 | Smith |
| 5,098,392 A | | 3/1992 | Fleischhacker et al. |
| 5,127,626 A | * | 7/1992 | Hilal et al. ............... 251/149.1 |
| 5,437,645 A | | 8/1995 | Urban et al. |
| 5,651,771 A | * | 7/1997 | Tangherlini et al. ........ 604/158 |
| 5,653,700 A | | 8/1997 | Byrne et al. |
| 5,792,112 A | | 8/1998 | Hart et al. |
| 5,836,914 A | | 11/1998 | Houghton |
| 5,921,968 A | * | 7/1999 | Lampropoulos et al. ..... 604/246 |
| 6,083,207 A | * | 7/2000 | Heck ......................... 604/256 |
| 6,220,859 B1 | * | 4/2001 | Hoffman ...................... 433/91 |
| 6,558,354 B1 | | 5/2003 | Howell |
| 6,589,262 B1 | | 7/2003 | Honebrink et al. |
| 6,966,896 B1 | * | 11/2005 | Kurth et al. ........... 604/167.06 |

FOREIGN PATENT DOCUMENTS

| | | |
|---|---|---|
| DE | 19826746 C1 | 11/1999 |
| EP | 0422631 A | 4/1991 |

OTHER PUBLICATIONS

European Search Report dated Oct. 12, 2005 for PCT Application No. PCT/US2005/020927.

* cited by examiner

*Primary Examiner*—Nicholas Lucchesi
*Assistant Examiner*—Theodore J. Stigell
(74) *Attorney, Agent, or Firm*—Vincent J. Serrao

(57) ABSTRACT

A catheter grip adapted to couple with an introducer or sheath holds a catheter in position while in use in a patient's body. The grip has a hub defining a channel through which the catheter extends, a pair of grip members that work with each other to hold the catheter body between them, a pair of separators to release the catheter body, and a pair of tabs for the doctor to actuate the separators. Each pair of the grip members and the separators is situated on a different diameter of a surface that extends across the channel and each grip member and separator is diametrically opposed to its mate. Movement between the grip members and the separators is coordinated in that as the grip members move toward each other the separators move away from each other, and vice versa.

19 Claims, 7 Drawing Sheets

CATHETER GRIP

FIELD OF INVENTION

This invention relates to catheters and catheter accessories, particularly, a device that holds a catheter in position while in use in a patient's body.

BACKGROUND OF THE INVENTION

Electrode catheters have been in common use in medical practice for many years. They are used to stimulate and map electrical activity in the heart and to ablate sites of aberrant electrical activity. In use, an electrode catheter is inserted into a major vein or artery, e.g., femoral artery, and then guided into the chamber of the heart which is of concern. The catheter should preferably be deflectable to permit proper positioning of the electrodes on its distal end within the heart.

Deflectable tip electrode catheters are well known. Such a catheter generally has a control handle at its proximal end for controlling deflection of the tip in one or more directions. For example, a particularly useful deflectable tip catheter is disclosed in U.S. Pat. No. Re. 34,502 to Webster, the disclosure of which is hereby incorporated by reference. This catheter comprises a puller wire that extends on-axis through an elongated reinforced catheter body and then off-axis in a deflectable tip portion. In this arrangement, longitudinal movement of the puller wire relative to the catheter body results in deflection of the catheter tip portion. Other examples of steerable catheters can be found in U.S. Pat. No. 5,431,168 to Webster entitled "Steerable Open-Lumen Catheter" and U.S. patent application Ser. No. 08/924,611 to Webster entitled "Omni-Directional Steerable Catheter," the disclosures of which are hereby incorporated by reference.

One drawback to catheters and perhaps especially deflectable catheters is the difficulty of maintaining a catheter in position while in the patient's body. That is, once a suitable tissue site has been located for treatment or evaluation, such as mapping, ablation or the like, the physician is often caught in a predicament with maintaining at least one hand on the catheter while attempting to record or otherwise mark the location of the tissue site. The problem may be greater with deflectable catheters which can store torsional energy and therefore unwind and shift when released from the doctor's grasp. With the heart chamber being a dynamic environment surrounded by moving tissue and blood flow, the target site, which may be relatively small to begin with, can be readily lost with the slightest movement in the catheter.

Because a catheter is typically used with an introducer or a sheath which facilitates the catheter's entry into the patient's body via a valve, it would be desirable to provide a catheter grip that attaches to the valve. Often with one hand already working the introducer or sheath, an attending doctor could then readily use that same hand to operate the catheter grip. Moreover, it would be desirable to bias the grip toward a closed or gripping configuration so that actuation of the grip involves minimal action on behalf of the doctor.

SUMMARY OF THE INVENTION

The present invention is directed to a catheter grip adapted to couple with a valve of an introducer or sheath and hold a catheter in position while in use in a patient's body. In one embodiment, the grip, which frees the hands of the attending doctor once he has closed the grip on the catheter, includes a hub defining a channel through which the catheter extends. The grip includes components for gripping the catheter and components to release the catheter.

To reach a target site within the patient's body, an elongated body of a catheter is passed through the channel and through the coupled valve into the patient's vein. The hub has a pair of grip members that work with each other to hold the catheter body between them, a pair of separators to release the catheter body, and a pair of tabs for the doctor to actuate the separators. Each pair of the grip members and the separators is situated on a different diameter of a surface that extends across the channel, such that the pairs of grip members and separators are offset from each other by a predetermined angle and each grip member and separator is diametrically opposed to its mate.

In one embodiment, the grip members and the separators are movable on tracks configured on the surface in alignment with the two diameters. The tracks have a female fitting portion which receives a male fitting portion configured on each grip member and separator and enables each grip member and separator to move toward and away from its mate across the surface. The predetermined angle offset between the tracks optimizes the wedge action of the separators on the grip members in separating the grip members to release the catheter body.

In another embodiment, the grip members are biased by an elastic member to move toward each other to clamp the catheter body. Interfacing ends of the grip members are notched and have a friction-inducing surface for a more secure hold on the catheter body. Moreover, interfacing ends of the grip members and the separators may be angled to facilitate the leverage action of the separators on the grip members.

DETAILED DESCRIPTION OF THE INVENTION

Figure 1:
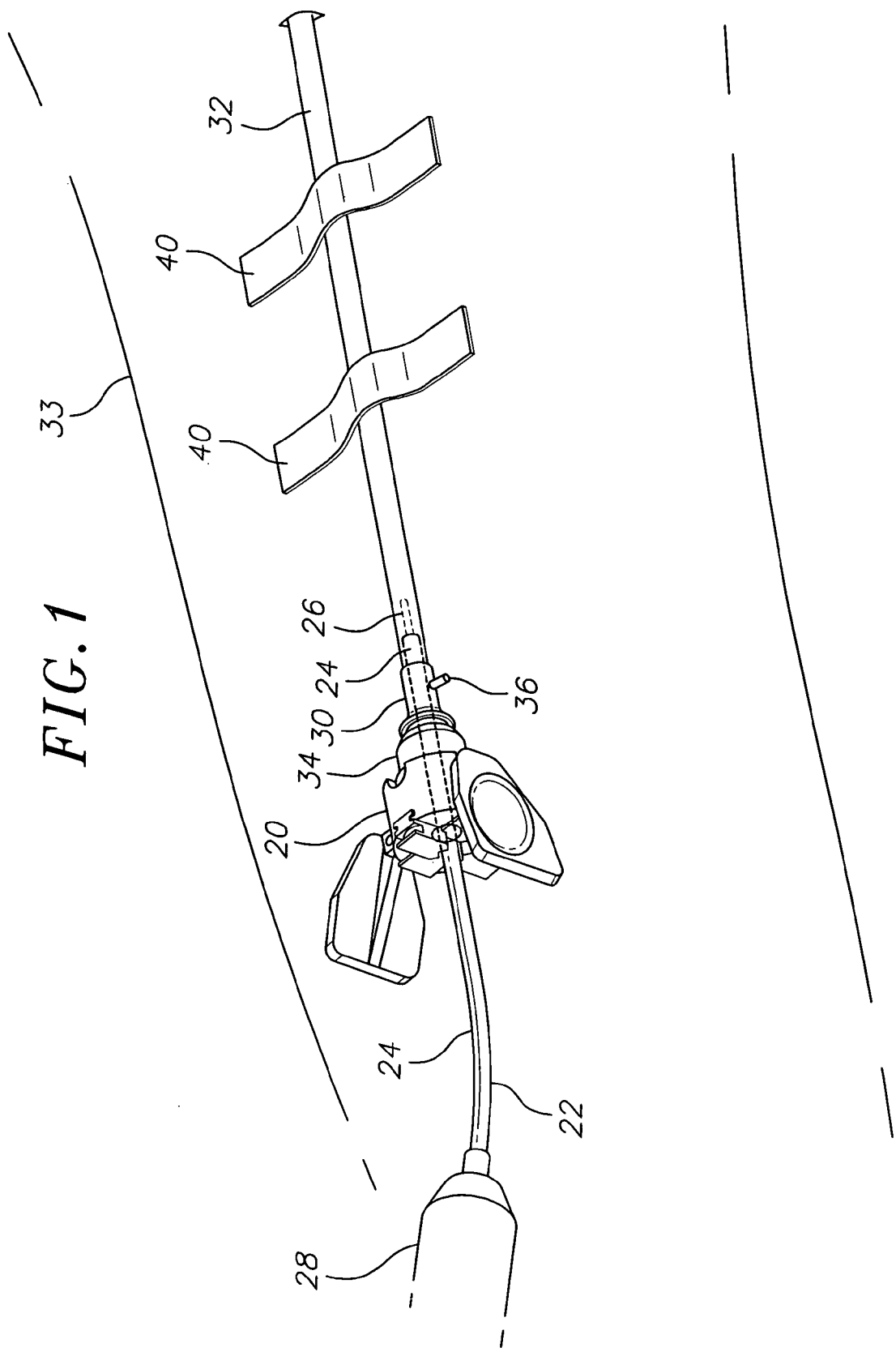
FIG. 1 is a perspective view of an embodiment of a catheter grip of the present invention for use with an introducer (or sheath) and a catheter.

FIG. 1 illustrates a catheter grip 20 in accordance with an embodiment of the present invention. The grip 20 is adapted to releasably grip and hold a catheter 22 in use in a patient's body for treatment or evaluation, such as mapping, ablation and the like. Once it is clamped on the catheter, the grip 20 effectively minimizes, if not prevents, the catheter from moving or shifting within the patient's body. As such, the grip 20 frees the hands of the attending doctor once he has closed the grip on the catheter. For purposes of the discussion herein, the catheter 22, as with most conventional catheters, has the elongated catheter body 24 that extends between a catheter tip section 26 and a control handle 28. The catheter body 22 and the catheter tip 26 are portions that generally enter the patient's body, whereas the control handle 28 remains outside the body.

The catheter grip 20 is adapted for use with an introducer or sheath 30 having a tubular needle 32 that is inserted into a patient's vein or artery, typically in a leg 33. Introducers and sheaths are generally known and can take on many different configurations. Most have a valve 34 that is provided at the proximal end of the needle. The valve may or may not have a side port 36 for the introduction of a fluid to the entry site of the tubular needle 32. Accordingly, the introducer or sheath (used interchangeably herein) is generally used to facilitate the entry of the catheter tip 26 (not shown) and body 24 into the vein by providing a prepared portal into the patient's body through the valve 34 and the needle 32.

Figure 2:
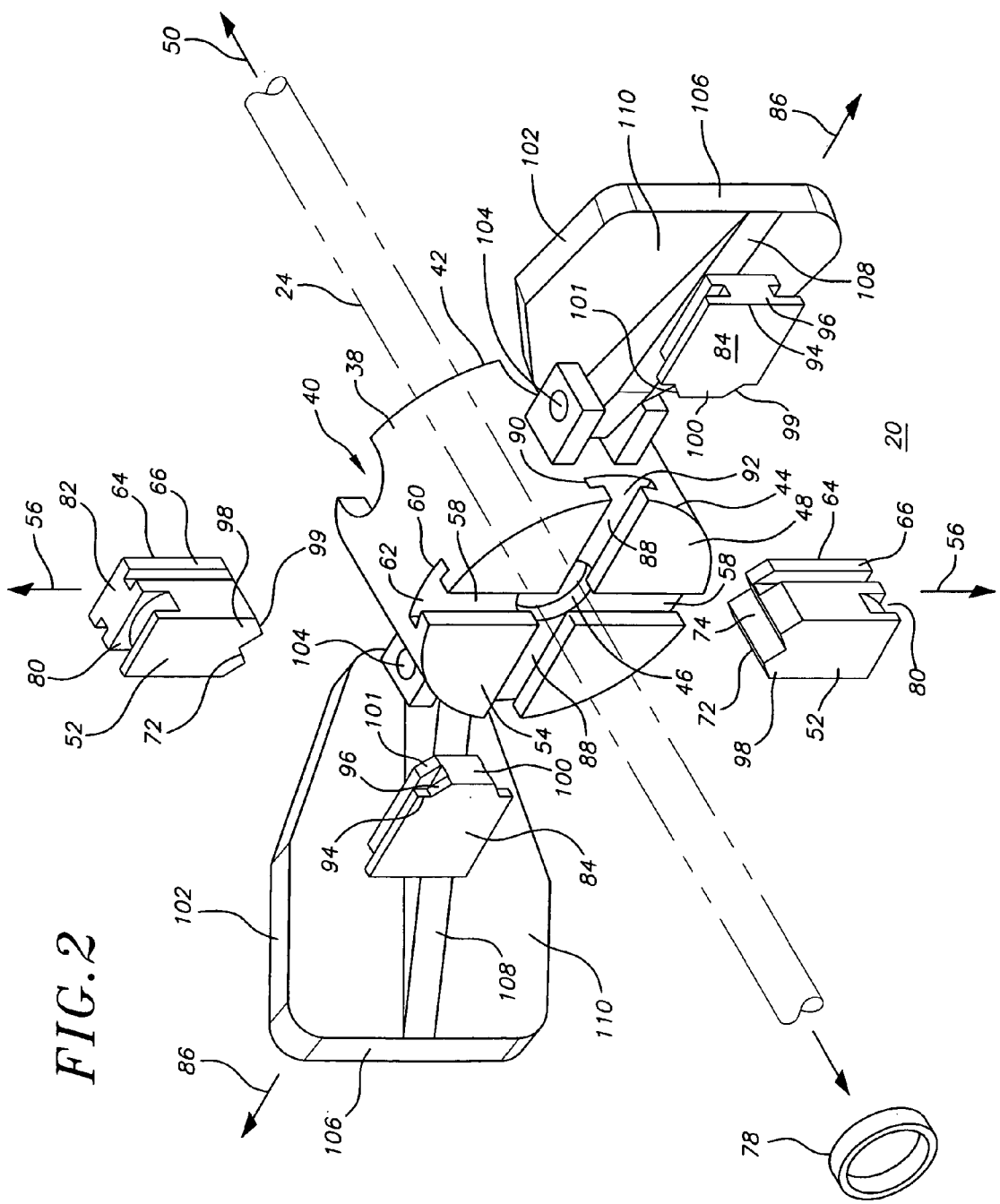
FIG. 2 is an exploded view of the grip of FIG. 1

Referring FIGS. 1 and 2, the grip 20 is configured as a cylinder or barrel which functions in part as a coupling hub 38 that attaches to the proximal end of the valve 34 before or, more preferably, after the introducer 30 has already been inserted and secured to the patient by conventional methods, such as medical tape and bandages 39. The valve 34 and the hub 38 are releasably coupled to the extent that inadvertent detachment is avoided but intentional decoupling is facilitated. In that regard, the valve and the hub can be snap-fitted, threaded, latched together and/or detachably coupled by other similar methods. In the illustrated embodiment, the valve and hub are frictionally engaged by means of a female fitting formed in the proximal end of the valve and a closely-conforming male fitting formed in the distal end of the hub. It is understood by one of ordinary skill in the art that the configuration, shape and/or size of the hub and the valve can vary. The grip 20 is preferably constructed of a suitably rigid material (including plastic, steel, synthetic or natural rubber, and the like, or combinations thereof) to accomplish its function of holding and maintaining the catheter in position in the patient's body.

Figure 3:
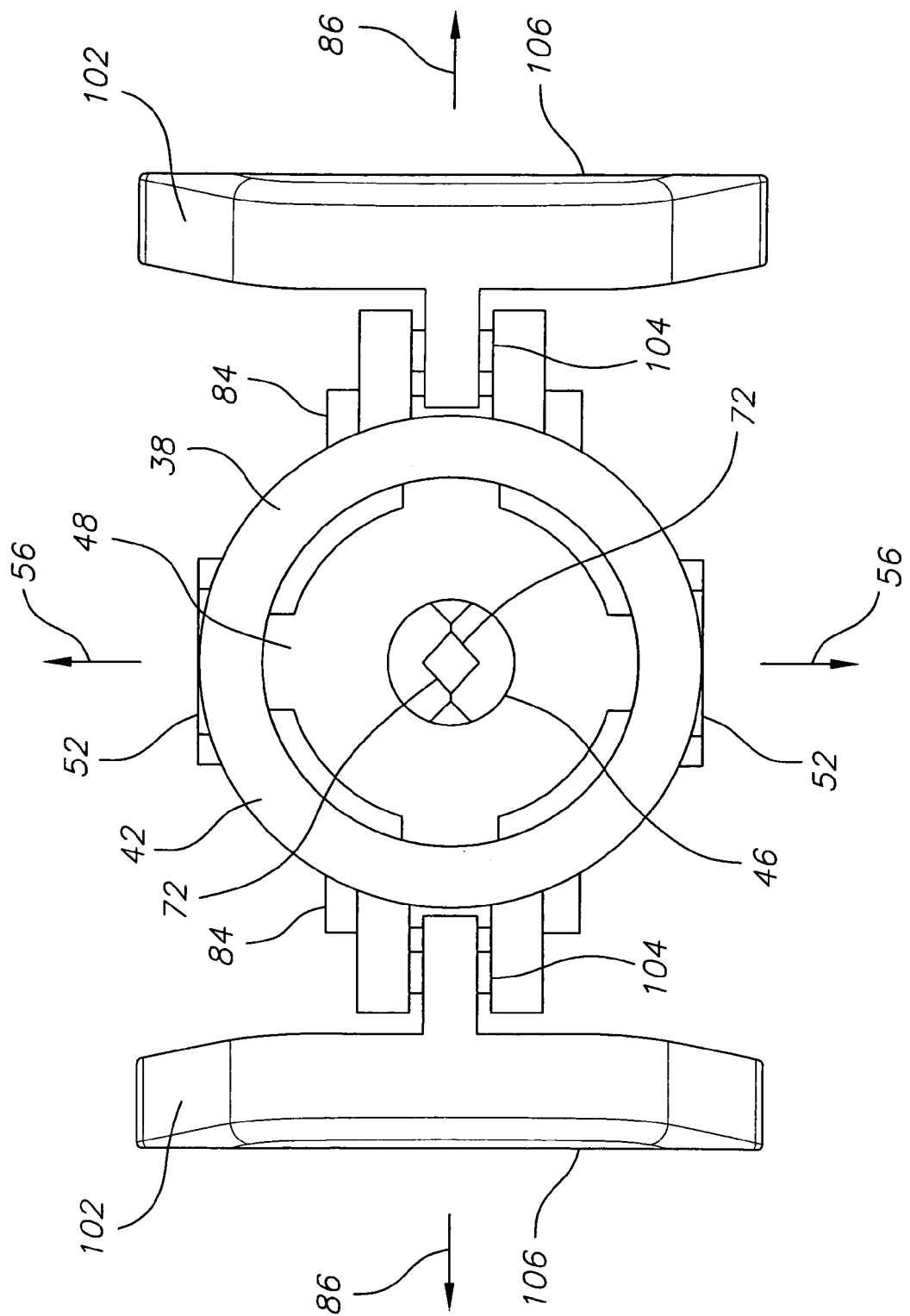
FIG. 3 is rear view of the grip of FIG. 1, the grip being shown in the closed position.

With the introducer 30 secured to the patient's body and the grip 20 coupled to the introducer at its proximal end, the catheter tip 26 and body 24 can be inserted through the grip and the coupled introducer for entry into the patient's body further through the needle 32. As best shown in FIGS. 2–3, the hub 38 is also configured with a channel 40 that extends between a distal end 42 and a proximal end 44, the latter of which has an aperture 46 formed in an end wall 48 that extends across the channel. The aperture 46 and the hub 38 are generally concentric about an axis 50 through the channel 40 and each is configured to permit the passing and generally free movement of the catheter tip section 26 and body 24 distally and proximally through the channel 40.

Figure 4:
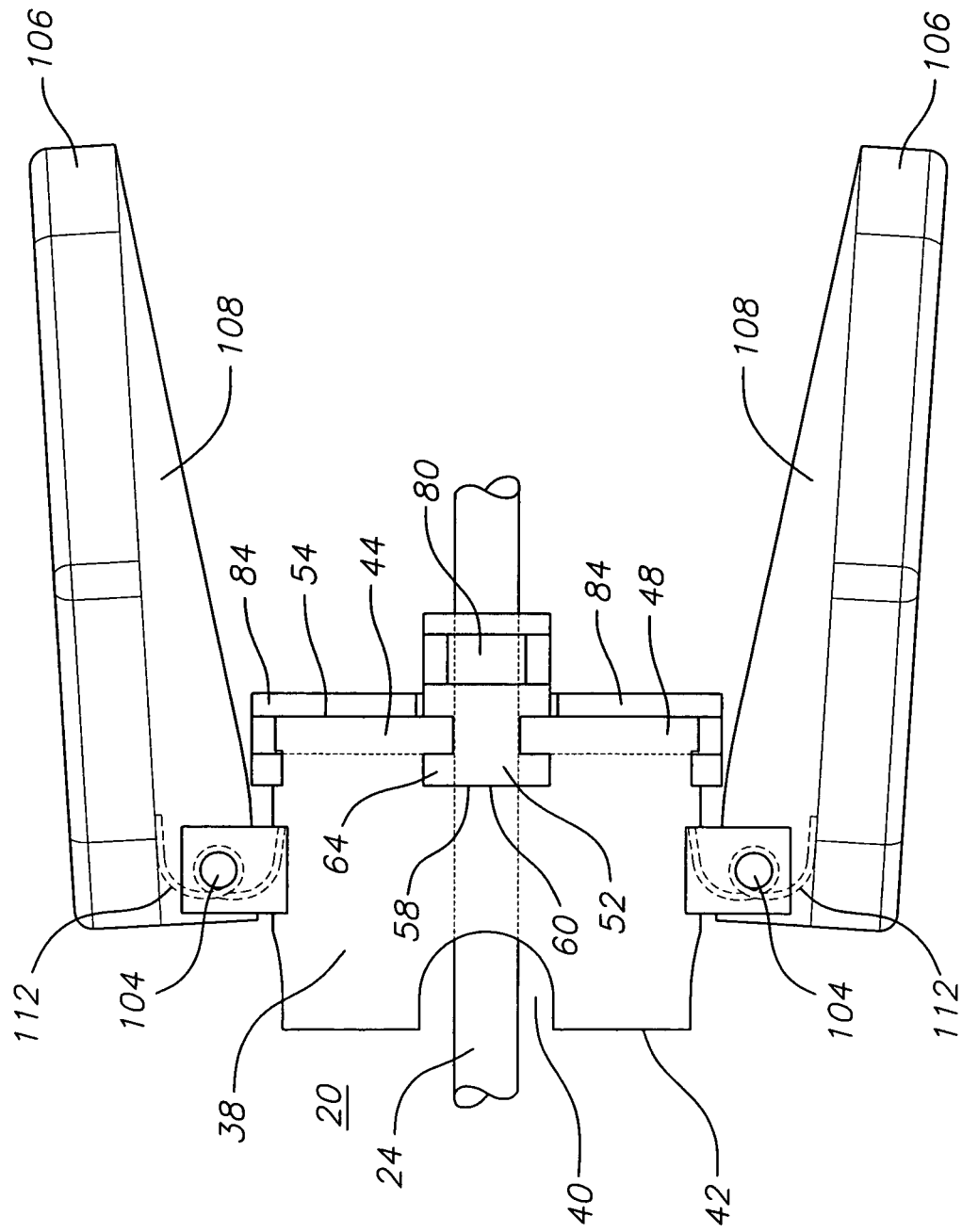
FIG. 4 is a top view the grip of FIG. 1, the grip being shown in the closed position.

In the illustrated embodiment, the grip 20 includes a pair of grip members 52 situated on a proximal surface 54 of the wall 48. The grip members 52 are aligned along a diameter 56 of the proximal surface 54 and face each other from across the aperture 46. In accordance with the present invention, the grip members 52 can move radially inward toward each other to clamp onto the catheter body 24 extending through the aperture 46 and the channel 40. To facilitate this movement, the grip members 52 travel on a first track 58 formed in the proximal surface 54 along the diameter 56, which is illustrated with a generally vertical orientation. The grip members 52 and the track 58 are engaged with each other by means of corresponding male and female fitting portions. Referring also to FIG. 4, the disclosed embodiment of the track 58 has a slot 60 with a T-shaped cross-section 62 which receives a ridge 64 with a T-shaped cross-section 66 formed in a distal surface 68 of each grip member 52. Guided by the track 58, the grip members 52 are slidable inwardly and outwardly along the diameter 56.

It is understood that the aperture 46 itself need not be (and is not) physically affected by movement of the grip members 52. It is therefore also understood that the aperture may be configured at any location along the length of the channel 40 and that the grip members 52 need not be in close proximity to nor proximal of the aperture 46. However, because the aperture 46 can guide the travel path of the catheter body 24 in the channel, it may be preferable in most instances that the grip members 52 and the aperture 46 be configured at least adjacent to each other along the channel 40. In the illustrated embodiment, the grip members and the aperture are in close proximity of each other and the grip members are immediately proximal of the aperture.

Figure 6:
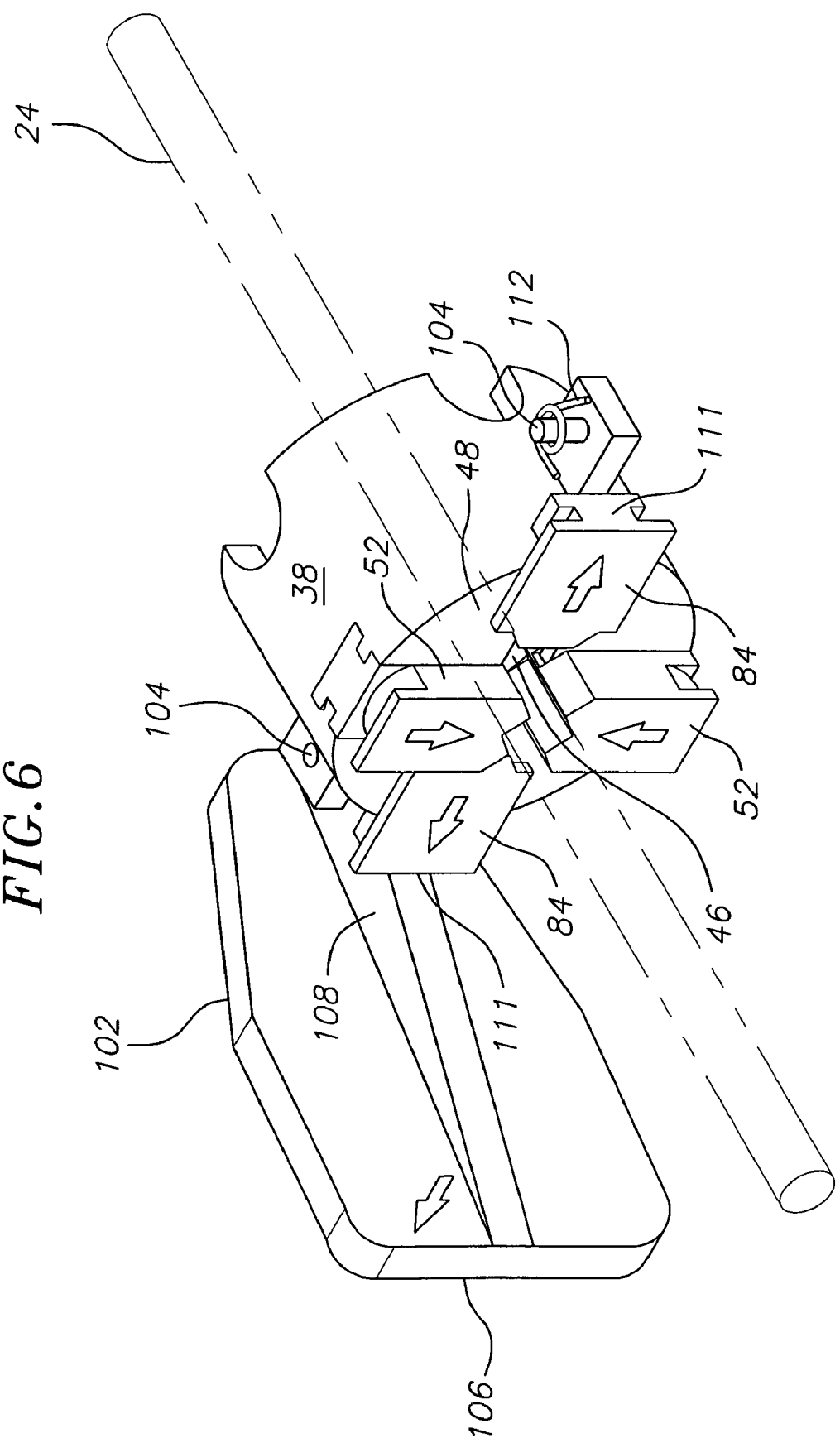
FIG. 6 is a perspective frontal view of the grip of FIG. 1, with parts broken away for clarity, the grip being shown in the closed position.

Referring to FIGS. 2 and 6, an inner end 70 of each grip member 52 is configured with a notch 72 so that the pair can have a more secure hold on the catheter body 24 between them. In particular, the notch 72 provides better conformity between the interfacing inner ends 70 and the circumference of the catheter body 24. Depending on the size, flexibility and/or elasticity of the catheter body, the inner ends (notched or otherwise) may or may not be in contact with each other when the grip members 52 are clamped on the catheter body 24. In any case, the grip members 52, having a greater frictional contact with the catheter body as provided by the notches, minimize if not prevent translational or rotational movement in the catheter body once released from the hands of the doctor. To that end, surface 74 of the notches 72 may be textured and/or covered with a friction-inducing material 76 (not shown). Once closed, the grip 20 is "hands-free" in minimizing the need for the doctor to hold the catheter body 24 in position for fear that the catheter may shift or move out of position.

In accordance with the present invention, the grip members 52 "rest" in a closed (or grip) position, as shown in FIGS. 3 and 6, under the bias of an elastic member or band 78 shown in FIG. 2. The elastic member sits in a groove 80 configured in an outer section 82 of each grip member 52. The elastic member 78 exerts around its circumference a force directed radially inward such that the grip members 52 are under a predetermined bias to move toward (if not to make contact with) each other and/or remain in the closed position until actively opened by the user.

Figure 5:
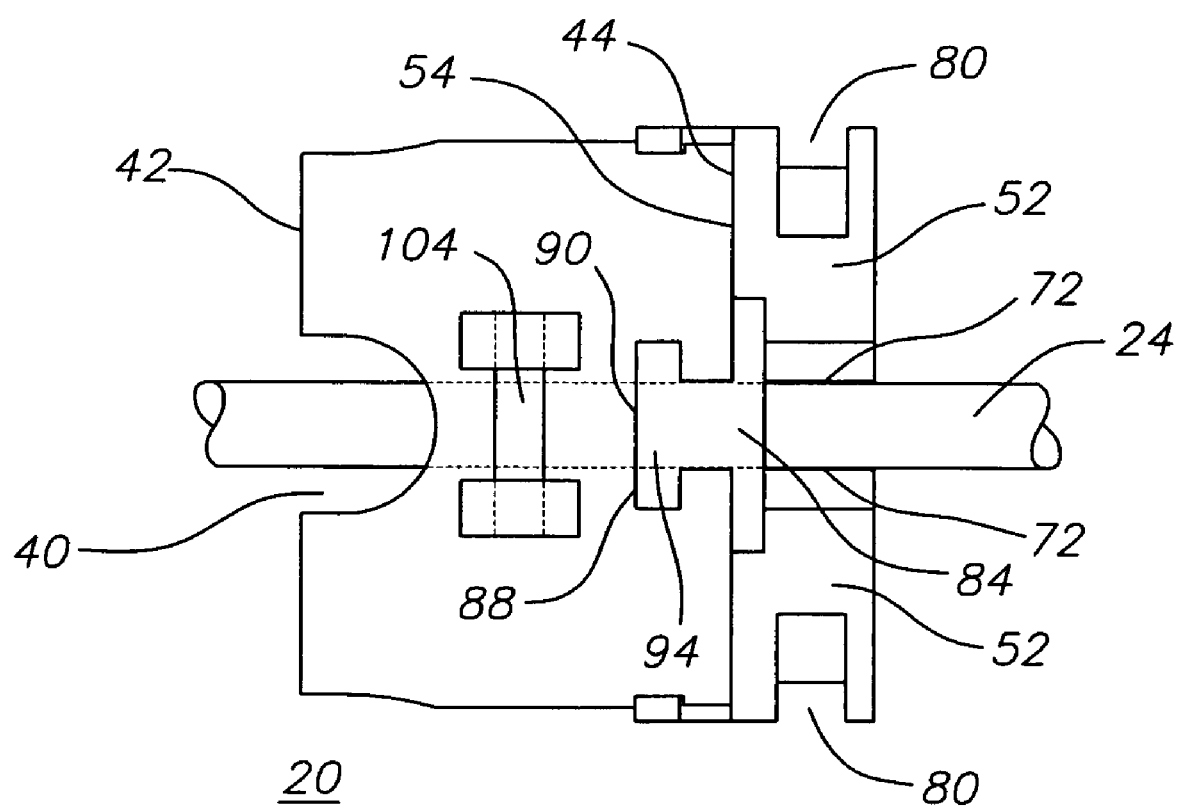
FIG. 5 is a side view of the grip of FIG. 1, with parts broken away for clarify, the grip being shown in the closed position.
Figure 7:
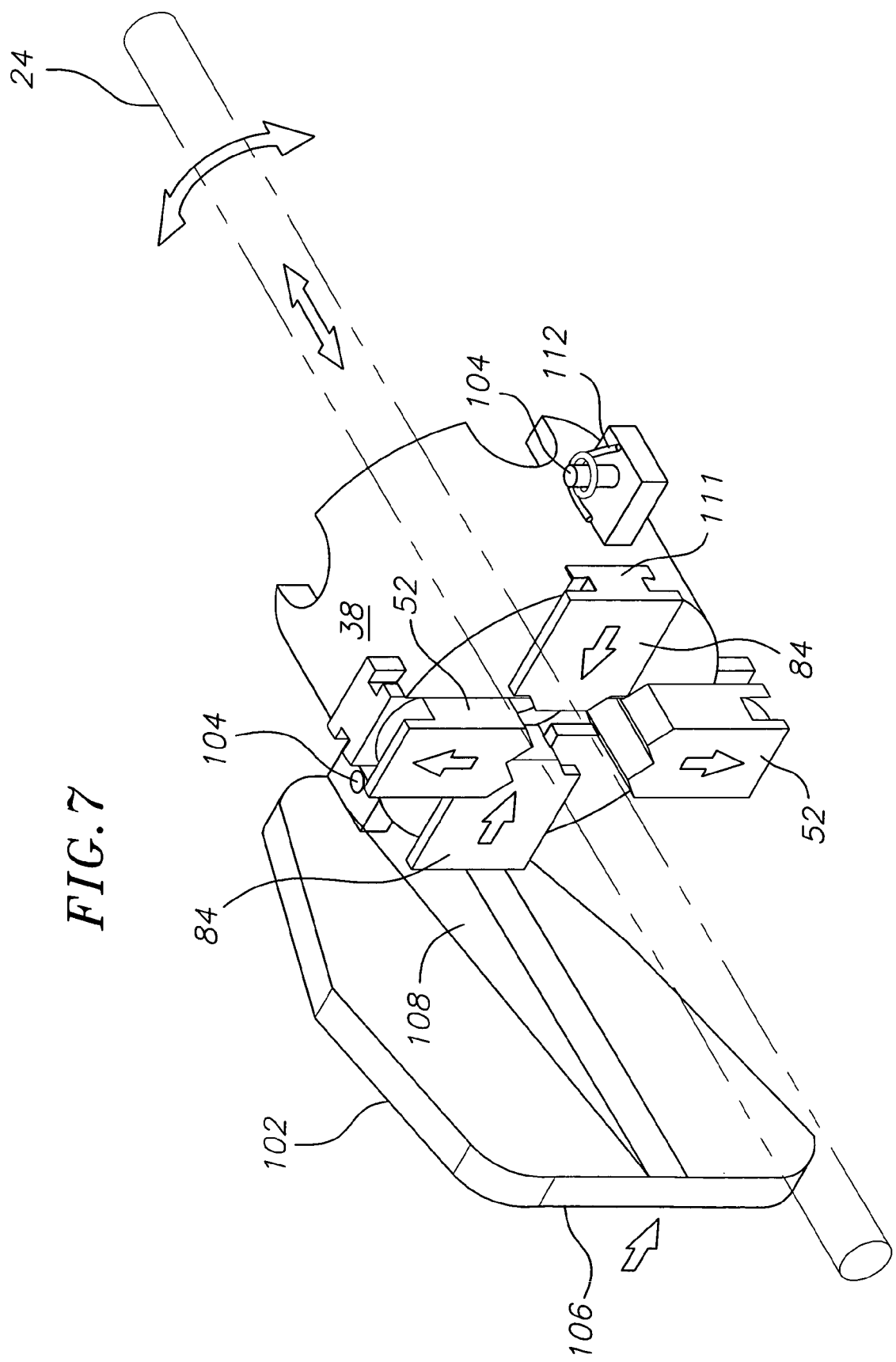
FIG. 7 is a perspective frontal view of the grip of FIG. 6, the grip being shown in the open or release position.
Figure 2:
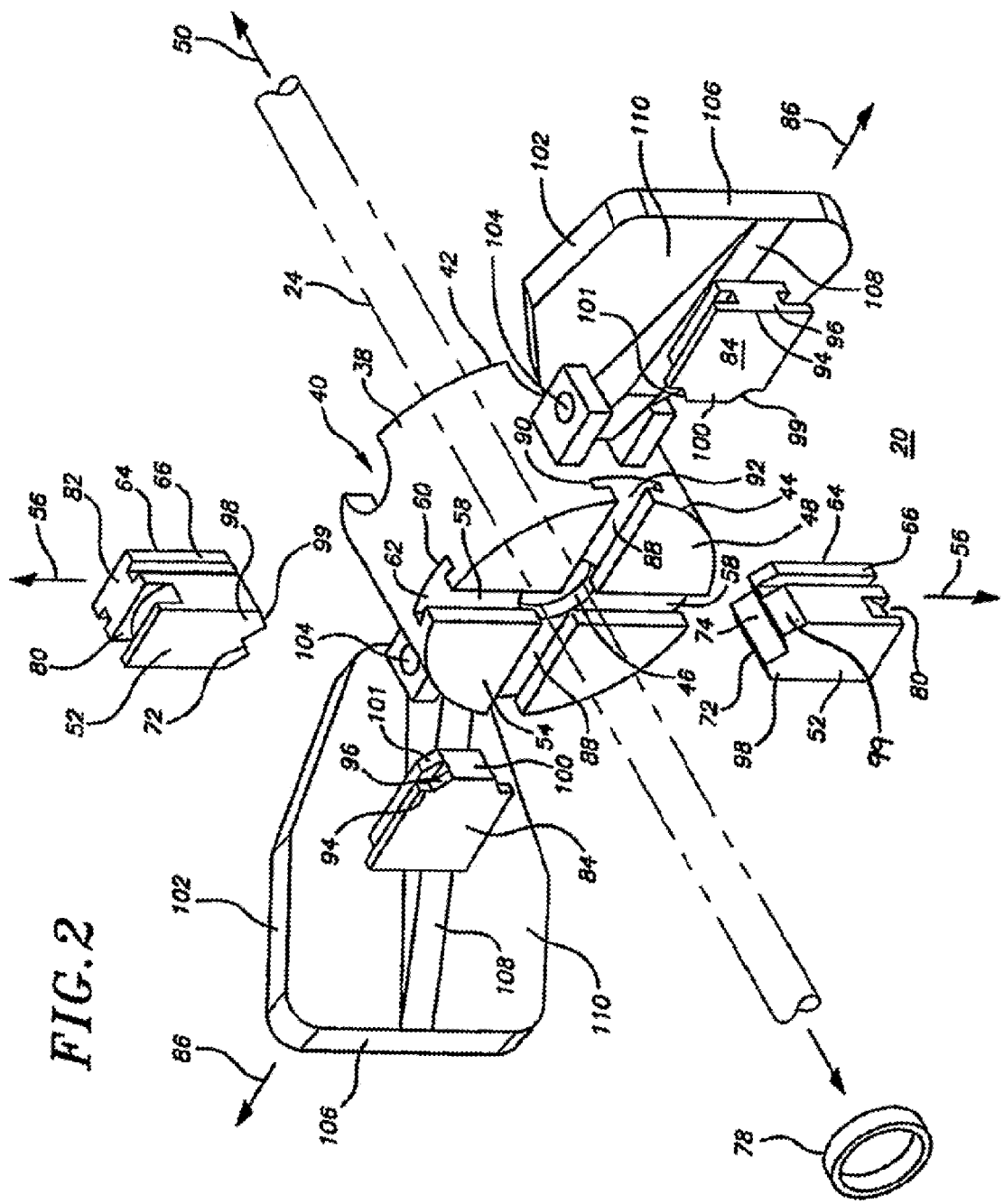
Figure 7:
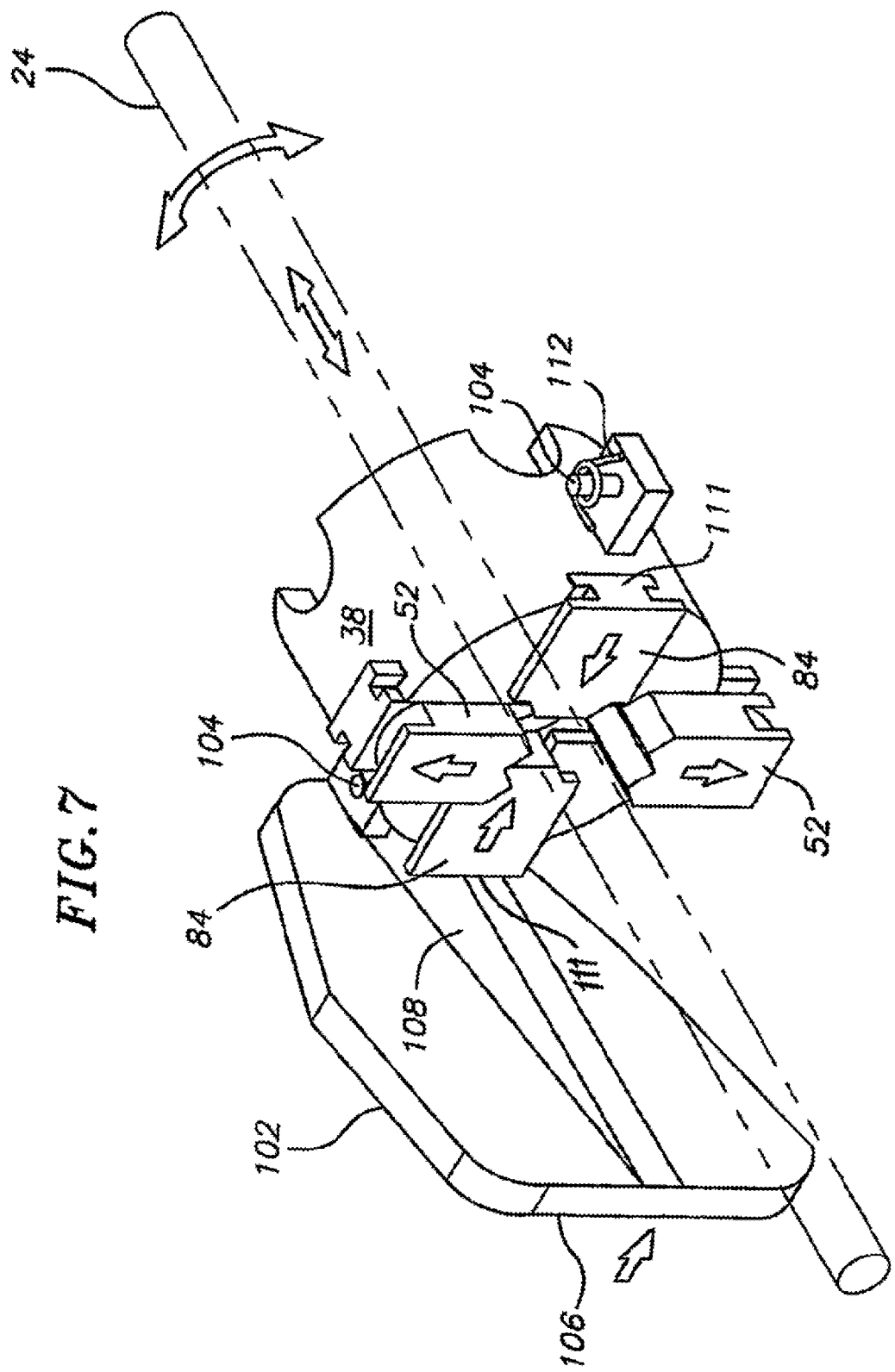

To open the grip members 52, the grip has a pair of separator or wedgers 84 that are also situated on the proximal face 54 but along a diameter 86 that is offset between about 60–120 degrees, and more preferably about 90 degrees, from the diameter 56 of the grip members 52. Like the grip members, the wedgers 84 face each other from across the aperture 46 and can move toward and away from each other. In accordance with the present invention, the catheter body 24 is released by the grip 20 when the grip members 52 are separated or driven away from each other, that is, radially outward, by the wedgers 84, as shown in FIG. 7. To facilitate this action, the wedgers 84 travel along a track 88 also formed in the proximal surface 54 along the diameter 86, best seen in FIG. 5, with a generally horizontal orientation. The wedgers 84 and the track 88 are engaged with each other by similar means of a male and female fitting portion. In the illustrated embodiment, the track 88 has a slot 90 with a T-shaped cross-section 92 which receives a ridge 94 with a T-shaped cross-section 96 formed in a distal surface of each wedger 84. Guided by the track 88, the wedgers 84 can slide inwardly and outwardly along the diameter 86 of the surface 54. And, because the wedgers 84 and the grip members 52 interact and are interdependent, as described below in further detail, they have portions that affect and/or contact each other and are therefore in close proximity of each other within the grip.

The wedgers 84, as the name implies, serve to wedge between and drive apart the grip members 52 in releasing the latter's hold on the catheter body 24. Inner ends 98 and 100 of the grip members 52 and the wedgers 84, respectively, are angled or chamfered at their corners 99 and 101, for example, at an angle ranging between about 30 and 60 degrees, and preferably at about 45 degrees, to facilitate this action. The convergence at the inner ends 100 of the wedgers 84 is limited; that is, the inner ends 100 are blunt so as not to protrude inwardly to the extent they contact or cause interfere with the catheter body 24.

For optimum leverage between the grip members 52 and the wedgers 84, the inner ends 98 and 100 can be angled at a complementary angle, for example, where the total of the angles of the inner ends equals about 90 degrees). However, it is understood by one of ordinary skill in the art that the slant or degree of angle of the inner ends may be varied for different efficiencies of operation. For example, a more obtuse angle may offer a different feel or tension in the operation of the grip 20, than would a more acute angle. Moreover, the angle (which may or may not be identical between the wedge members 84 and the grip members 52) may also depend on or relate to the offset angle between the tracks 58 and 88.

In any case, the grip members 52 are moved toward each other for a closed or grip position (FIG. 6), and away from each other for a release position (FIG. 7). Correspondingly, the wedge members 84 are moved toward each other for a wedge position (FIG. 7), and away from each other for a separated position (FIG. 6). In view of the foregoing description, it is clear that the movements of the pairs of grip members 52 and wedge members 84 are coordinated and interdependent in a manner whereby one pair moves toward each other as the other pair moves away from each other.

Movement of the wedge members 84 toward each other to release the catheter body 24 is actuated primarily by means of a pair of tabs 102. The tabs are pivotably attached to hinges 104 provided on the hub 38 and situated generally on the diameter 86 in alignment with the wedgers 84. The hub may be indexed to facilitate this alignment. In the illustrated embodiment, the hinges 104 are distal of the surface 54 and the tabs 102 extend slightly proximally from the hub 38 with their free ends 106 separated by a maximum distance which decreases to a minimum distance when the tabs are squeezed together by the user. When squeezed, the tabs act on the wedgers 84 through an angled ridge or cam 108 provided on an inner surface 110 of each tab. As can be seen in FIG. 7, as the free ends 106 approach each other, each cam 108 engages an outer end 111 of an adjacent wedger 84 to drive it inwardly toward its mate.

In accordance with the present invention, the tabs 102 are biased away from each other by leaf springs 112 (best seen in FIGS. 6 and 7) such that the tabs spring apart when the user stops squeezing. The bias of the elastic member 78 around the grip members 52 also tends to urge the wedgers 84 to move away from each other. The wedge members 80 therefore "rest" apart from each other (at their maximum separation) until they are moved toward each other by the tabs. It is understood that the tabs may be biased to spring apart by other means. To that end, the leaf springs 112 may be connected or integrated into a single piece extending across the channel 40 to leverage the tabs 102 against each other so they move in a coordinated manner, that is, similarly and coincidentally.

Advantageously, a doctor can use the very hand working the introducer 30 to actuate the tabs 102, and do so without changing hand position. The grip 20 therefore provides improved ergonomics for the doctor, if not a more versatile working environment in which he has more mobility, or at least more freedom with his hands once the grip 20 is closed on the catheter body 24.

In operation, the grip 20 rests in the closed position, with the grip members 52 being in contact with each other under the bias of the elastic member 78 and the wedgers 84 separated and generally free from compression by the tabs 102 (FIG. 3). By squeezing the tabs 102, the doctor opens the grip 20 so that he can pass the catheter tip and body through the aperture 46 and into the introducer 30. As long as the tabs 102 are squeezed, the cams 108 press on the wedgers 84 inwardly keeping the grip members 52 wedged apart. The catheter body 24 can then be advanced by rotation and/or translation to reach the target site inside the patient's body (FIG. 7).

After the target site has been reached and the catheter body 24 is in position, the doctor releases the tabs 102 which spring back under the force of the leaf spring 112. Without any compressive force pushing the wedgers 84, they are forced outwardly by the inwardly-moving grip members 52 acting under the force of the elastic member 78. As the grip members 52 clamp on the catheter body 24 (FIG. 6), the notches 72 close around the circumference of the catheter body and the friction-inducing surface 74 securely holds the catheter body 24 to resist sliding or twisting caused by any stored torsional or coiled energy. To adjust or reposition the catheter body 24, the doctor re-squeezes the tabs 102 to re-separate the grip members 52. Indeed, release of the grip 20 to separate the grip members 52 can be done at any time and be momentary or of a longer duration as desired by the doctor.

It is understood by one of ordinary skill in the art that configuration of the grip and its components can be varied. For example, the grip can be biased toward the open position, such that a band acts to close the wedge members with a leaf spring and/or the tabs separating the grip members. Furthermore, the tabs may be take on a different shape or extend from the hinge at a different angle.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A grip for use with a catheter having an elongated catheter body, comprising:
   a hub with a channel through which the catheter body can extend, the hub having a surface extending across the channel;
   a first track configured along a first diameter of the surface, a second track configured along a second diameter of the surface, said first and second diameters being angularly offset from each other;

a pair of grip members adapted to move toward each other along said first track and hold between them the catheter body;

a pair of separators adapted to move toward each other along said second track and separate the grip members to release the catheter body; and a pair of actuators configured to drive the separators toward the grip members in response to manipulation by a user.

2. A catheter grip of claim 1, wherein the actuators are biased against driving the separators toward the grip members.

3. A catheter grip of claim 1, wherein the grip members move toward each other as the separators move away from each other.

4. A catheter grip of claim 1, wherein the separators move toward each other as the grip members move away from each other.

5. A catheter grip of claim 1, further comprising a bias member biasing the grip members toward each other.

6. A catheter grip of claim 1, wherein said tracks are angularly offset at a predetermined angle of about 90 degrees.

7. A catheter grip of claim 1, wherein said surface is formed on a wall extending across the channel, the wall having an aperture through which the catheter body extends.

8. A catheter grip of claim 1, wherein the hub is adapted to be coupled with an introducer or sheath.

9. A catheter grip of claim 1, wherein one of the first track and the grip members has a male engagement portion and the other of the first track and the grip members has a corresponding female engagement portion, wherein the male engagement portion is received in the female engagement portion.

10. A catheter grip of claim 1, wherein one of the second track and the separators has a male engagement portion and the other of the second track and the separators has a corresponding female engagement portion, wherein the male engagement portion is received in the female engagement portion.

11. A catheter grip of claim 1, wherein inner ends of the separators and the grip members are angled.

12. A catheter grip of claim 1, wherein inner ends of the grip members have a notch.

13. A grip for use with a catheter having an elongated catheter body, comprising:

a hub with a channel through which the catheter body can extend, the hub having a surface extending across the channel, the hub adapted to couple with an introducer or a sheath;

a first track configured along a first diameter of the surface, a second track configured along a second diameter of the surface, said first and second diameters being generally perpendicular to each other;

a pair of grip members adapted to move toward each other along said first track and hold between them the catheter body;

a pair of separators adapted to move toward each other along said second track and separate the grip members to release the catheter body; and a pair of actuators responsive to manipulation by a user to drive the separator toward the grip members, each actuator having a cam surface acting on an outer end of a different separator;

wherein the grip members are biased toward each other and the actuators are biased against driving the separators toward the grip members.

14. A grip of claim 13, wherein the grip is coupled to a proximal end of the introducer or sheath.

15. A grip of claim 13, wherein the actuators are adapted to be squeezed toward each other by the user.

16. A grip of claim 15, wherein the actuators are hinged to the hub generally along the second diameter.

17. A grip of claim 16, wherein the actuators are configured to be manipulated by one hand of the user.

18. A grip of claim 13, wherein the surface is configured on a wall extending across the channel, the wall having an aperture through which the catheter body extends.

19. A grip of claim 18, wherein the wall is at a proximal end of the hub and the grip members and the separators are proximal of the aperture.

* * * * *

UNITED STATES PATENT AND TRADEMARK OFFICE
CERTIFICATE OF CORRECTION

| | | |
|---|---|---|
| PATENT NO. | : 7,104,982 B2 | |
| APPLICATION NO. | : 10/871677 | |
| DATED | : September 12, 2006 | |
| INVENTOR(S) | : McDaniel | |

It is certified that error appears in the above-identified patent and that said Letters Patent is hereby corrected as shown below:

On the Title Page

Item (73) Assignee    Insert --(73) Assignee: Biosense Webster, Inc. Diamond Bar, CA (US)--

In the Drawings

FIG. 2, Sheet 2 of 7, Ref. No. 99    Delete Drawing Sheet 2 and substitute therefore the Drawing Sheet, cosnisting of Fig. 2, as shown on the attached page FIG. 7, Sheet 7 of 7, Ref. No. 111    Delete Drawing Sheet 7 and substitute therefore the Drawing Sheet, consisting of Fig. 7, as shown on the attached page Signed and Sealed this Twelfth Day of June, 2007

JON W. DUDAS
*Director of the United States Patent and Trademark Office*